United States Patent [19]

Urquhart

[11] Patent Number: 5,079,006
[45] Date of Patent: Jan. 7, 1992

[54] PHARMACEUTICAL COMPOSITIONS CONTAINING A MAGNETICALLY DETECTABLE MATERIAL

[75] Inventor: John Urquhart, Palo Alto, Calif.

[73] Assignee: Aprex Corporation, Fremont, Calif.

[21] Appl. No.: 218,733

[22] Filed: Jul. 13, 1988

[30] Foreign Application Priority Data

Jul. 15, 1987 [DE] Fed. Rep. of Germany ....... 3723310

[51] Int. Cl.$^5$ ............................................. A61F 13/00
[52] U.S. Cl. ................................. 424/422; 600/12; 424/426; 424/436
[58] Field of Search ...................... 424/422–426; 600/12

[56] References Cited

U.S. PATENT DOCUMENTS

| | | | |
|---|---|---|---|
| 2,671,451 | 3/1954 | Bolger | 600/12 X |
| 3,474,777 | 10/1969 | Figge et al. | 600/12 X |
| 3,608,549 | 9/1971 | Merrill | 424/426 X |
| 3,625,214 | 12/1971 | Higuchi | 128/260 |
| 4,005,699 | 2/1977 | Bucalo | 600/12 |
| 4,106,488 | 8/1978 | Gordon | 600/12 X |
| 4,136,683 | 1/1979 | Gordon | 600/12 X |
| 4,331,654 | 5/1982 | Morris | 600/12 X |
| 4,345,588 | 8/1982 | Widder et al. | 600/12 |
| 4,381,780 | 5/1983 | Holloway | 424/438 |
| 4,501,726 | 2/1985 | Schröder et al. | 600/12 X |
| 4,652,257 | 3/1987 | Chang | 600/12 X |
| 4,654,165 | 3/1987 | Eisenberg | 436/56 X |
| 4,729,892 | 3/1988 | Beall | 436/806 X |
| 4,849,210 | 7/1989 | Widder | 436/806 X |
| 4,863,715 | 9/1989 | Jacobsen et al. | 436/806 X |

FOREIGN PATENT DOCUMENTS

0052719 4/1979 Japan ................................. 424/423

*Primary Examiner*—Thurman K. Page
*Assistant Examiner*—Leon R. Horne
*Attorney, Agent, or Firm*—Irell & Manella

[57] ABSTRACT

A pharmaceutical preparation is provided for oral or anal administration containing, in addition to a selected pharmacologically active agent, at least one magnetic material capable of reacting to an externally acting magnetic field of an electronic monitoring device, so that after administration to a patient, a signal is produced that is selectively detectable by such a monitoring device, thus providing information on whether the preparation has been taken or not by the patient and/or facilitates locating the preparation or the magnetic material in the region of the gastrointestinal tract of the patient.

15 Claims, 4 Drawing Sheets

PHARMACEUTICAL COMPOSITIONS CONTAINING A MAGNETICALLY DETECTABLE MATERIAL

TECHNICAL FIELD

The invention relates generally to pharmaceutical compositions for oral or anal administration, and more particularly relates to such compositions having at least one magnetically detectable material incorporated therein.

BACKGROUND

There has already been considerable discussion in the medical literature concerning the problems involved with respect to the willingness, obedience and conscientiousness of the patients to take, in true conformity with the prescribed dosage and at the specified times, the medicines or drugs prescribed to them by the physician in charge.

From the said literature, it is possible to infer essentially the following:

1. There exists a significant minority of patients who make major mistakes in the "self-administration" of the prescribed drugs.
2. These mistakes are made more or less regardless of the seriousness or virulence of the respective disease.
3. Judging by experience, the patients generally so behave as to hide or conceal from their physicians any errors they have made with respect to the dosage or to the taking of drugs; in this connection it can also be stated that, on the basis of the behavior in medical terms and of the diagnostic acumen, most patients are actually successful in being able to conceal from the physicians in charge the nature and extent of the dosage mistakes or errors that they have made.
4. The error which generally occurs most frequently with respect to the drug dosage consists in failing or neglecting to take the prescribed drug.
5. A secondary dosage error which occurs less frequently and with less probability is generally one which consists in forgetting that the specified dose has already been taken, so that it is taken once again after approximately one hour or a longer time interval has elapsed.

Because of these circumstances, it is naturally extremely desirable from the therapeutic viewpoint to search for means and ways which ensure the following:

1. Monitoring of the patient community with respect to its behavior in the taking and dosage of the medicines prescribed to it by the physician.
2. Improvement of the behavior of the patients with respect to the dosage and taking of the drugs.
3. Minimization of the therapeutic consequences due to errors that the patients make in dosage.
4. Minimization of the probability that the physicians in charge will then misinterpret the errors made by the patients with respect to dosage and taking of medicines as:
   a) failure of the expected effectiveness of the drug;
   b) necessity for prescribing a larger dose than before;
   c) necessity for prescribing an additional drug;
   d) necessity for prescribing a stronger drug than the first;
   e) worsening or deterioration of the condition of the patient, and/or
   f) wrong diagnosis of the condition of the patient.

The mistakes and errors made by the patients with respect to the "self-administration" of the drugs prescribed to them can naturally lead to an unnecessary aggravation of the costs, time, suffering and risk to which the patient is exposed in achieving a cure or an alleviation of his illness. Accurate monitoring and checking of the drugs actually being taken would therefore lead to a great improvement as regards the quality of the therapy which is achievable with the available medicines.

According to the prior art, there already exist various means and ways of monitoring "self-administration" by the patients of the drugs intended, e.g., for oral application, but these known means and ways with few exceptions are all to be described as indirect, more precisely inasmuch as they do not provide real evidence that a prescribed medicine has actually been taken in the specified dosage. Moreover, in cases in which various strengths of the dosage are available for the patients, these known measures are not able to reveal in which dosage strength the medicine has been taken by the patient.

The currently available methods and techniques for monitoring of the oral taking of drugs can be divided into two categories: a) the "continuous" category; and b) the "intermittent" category.

In the continuous category, there already exists a number of applications of electrical and mechanical means which are used for the establishment or the initiation of appropriate measures if an oral form of application, e.g., pill, tablet or capsule, has been removed from its associated packaging. In this connection, the following is to be understood by "appropriate measures": the recording of the time, the tripping of an alarm or the transmission of a signal to a monitoring device, disposed, for example, in a remote location, or to a third person occupying a remote location.

However, by none of the methods explained above is it really possible to observe or confirm in which strength or dosage a medicine has been taken, if at all, by the patient.

Furthermore, various measures for observing or ascertaining dosage errors are known in the intermittent category. Such measures consist in, for example, intermittently taking samples of the blood, of the urine or of other body fluids of the patient and of analyzing these samples, in order to directly determine either the drug itself or a metabolite of the drug or very specific chemicals, the presence of which unequivocally proves that the drug in question has been taken by the patient.

By means of such measures and methods, it can be established that the drug in question has actually been taken, and more precisely at some certain time and in some certain dose, although it is not possible therewith exactly to specify "when" the medicine has been taken or "how much" of the medicine has been taken. Thus, these known methods suffer from the disadvantages that they are not suitable for extrapolation of occasional measurements or determinations on a continuous recording of when the preparation or drug has actually been taken.

A further known method for establishing whether a patient has forgotten to take a medicine in the specified dose consists in monitoring the opening and closing of the drug package or the removal of a medicine dose from the package by the patients, for example according to West German Patent 3,335,301 or West German Offenlegungsschrifts 3,530,356 and 3,504,431.

However, it is not even possible by means of these known methods to provide proof that the specified dose has actually been taken by the patient, but therewith it can be established only whether or not the drug package had been opened and not whether the medication was actually taken by a patient.

SUMMARY OF THE INVENTION

With regard to the problems and difficulties explained in the preceding with respect to the monitoring of the "self-administration" of drugs by the patients, and especially with respect to the continuity of such monitoring, the object of the present invention is now to provide a pharmaceutical preparation of the initially mentioned type, by which reliable and unequivocal information can be obtained on whether the preparation or drug prescribed by the physician has actually been taken or not by the patient, possibly supplemented by the additional items of information regarding in which does and/or at what time ingestion occurred and/or where the preparation can be located in the region of the gastrointestinal tract.

This object is achieved according to the invention in a pharmaceutical composition for oral or anal administration, by incorporating therein, in addition to a selected pharmacologically active agent, at least one magnetic material therein.

The invention further relates to a process for production of such a pharmaceutical composition.

The invention also relates to a method for monitoring a patient's drug dosage compliance, comprising, after a health care professional has prescribed administration of a pharmaceutical composition to a patient, the composition formulated so as to contain a detectable magnetic material, detecting the presence or absence of the magnetic material in the patient's body.

DETAILED DESCRIPTION OF THE INVENTION

By the invention there are therefore provided special pharmaceutical means, which contain, in addition to the necessary active substance or substances and the like in an appropriate extent, an appropriate size and an appropriate form, at least one magnetic material, by means of which a quantitative determination is precisely ensured of whether a prescribed means (possibly also at which time and possibly in which dose) has been taken or not by a patient. If yes, it is also possible even to locate the preparation or the magnetic material in the gastrointestinal tract.

For this purpose there is merely needed an external magnetic field, especially an alternating magnetic field, which is generated by the electronic monitoring device and, when the patient, after having taken the drug in the specified dose, moves into the region of this magnetic field or places himself in it or passes through it, then, as a result of the magnetic properties of the material contained in the drug and as a result of a reversal caused hereby of the magnetic polarity of the magnetic field, specific disturbances are generated or induced in this field, such that these disturbances are detectable by means of an appropriate receiver of the monitoring device, from which the evidence of the taking of the medicine can be obtained.

The electronic monitoring device, which is provided with a means for magnetic-field generation and a receiving means for the signal output, represents a separate apparatus which, for example, can be carried by the patient himself or else can be mounted in an object with which the patient comes into contact daily, for example in a bed, a favorite chair, a table at which the meals are consumed, an automobile seat, a door panel of the automobile, a toilet seat and many others of the like.

In this connection it can be desirable to provide more than one monitoring device in the living environment of the patient, e.g., one or more devices in the home or one or more devices at the workplace and/or in the automobile, in each case as a function of the living conditions and the lifestyle of the patient in question. Particularly also in the clinical environment, however, such electronic monitoring devices can also be provided, especially for operation by medical staff or nursing staff.

In the case of the drug according to the invention, it is further ensured that a distinction can be made between the undissolved and the dissolved state of the drug, the basis being that characteristic of materials with magnetic properties, especially resonance properties, wherein they react differently to an externally acting magnetic field depending on whether the materials or the elements formed therefrom are present in a condition which is magnetically undetectable or is detectable in different manner (e.g., weakly) or which is magnetically detectable (e.g., strongly detectable). In such a detectable condition, the resonance properties, for example, of the magnetic material become fully effective. Such a condition is reached in particular if the applied preparation has dissolved in, for example, the gastrointestinal tract (GI tract). Consequently, a distinction is ensured between, for example, a medicine taken by a patient and a medicine being carried by him in his pocket.

In other words, a magnetic material made, for example, in the form of a wire or tape or strip or film which is folded in zigzag manner or bent in helical manner or assembled in coiled or rolled manner will lead to initiation of a signal which is only very small or not even existent, whereas the magnetic material present in the unfolded or unrolled condition will generate a relatively strong signal, from which it can be concluded unequivocally that the preparation containing the originally rolled, folded or otherwise tightly assembled material strips or the like has dissolved in the GI tract and permitted opening of this strip.

Preferably, the magnetic material added to the preparation consists of a magnetically soft or an amorphous material, especially of an amorphous metal, such as, for example, iron, boron, an iron-silicon-boron-carbon compound, or the like. The amorphous forms of iron, boron and other metals are known to have no toxicity.

Preferably, a magnetic material is selected the magnetization curve or hysteresis loop of which exhibits a large Barkhausen instability. Such a magnetization curve is characterized by significant abrupt changes or by a regenerative reversal of the magnetic polarization if the applied preparation or drug is brought into the externally acting magnetic field and exposed to the positive and negative amplitudes of this field. The response behavior, to such abrupt reversals of polarity, of the magnetic element contained in its detectable condition in the preparation is revealed in particular in the generation of strong harmonic oscillations, which can easily be distinguished from the response behavior of other magnetic objects that can also be located with the range of the generated magnetic field. The use of materials of this type is known in, for example, electronic theft-monitoring systems (see West German Offenlegungsschrift 3,541,536). For maintenance of its magnetic properties in the detectable condition, the material can have such a composition that it cannot be dissolved or attacked by the gastric juices or enzymes or else it can be coated with a protective layer which cannot be dissolved or attacked by the gastric juices or enzymes. Because of these features, it is ensured that the magnetic material either with or without a protective layer is especially biologically inert, and above all, however, nontoxic.

Preferably the element formed from the magnetic material can be either embedded in the respective form of administration of the preparation, such as, for example, pill, lozenge, table, film- or membrane-coated tablet or capsule, sugar-coated pill, suppository or the like or introduced into a coating of these respective forms of administration.

Furthermore, magnetic materials selected advantageously as a function of the specific type of the preparation can be provided with different properties and/or with different geometric shapes, at least one of these materials being added in each case to a very specific preparation or the special forms of application thereof. Consequently, the possibility exists of detecting appropriately different signals and thus of distinguishing different preparations or medicines from each other, i.e., of detecting different medicines in the body of the patient in question. Moreover, it is even possible, in the use of a number of magnetic materials, each with different properties, in one and the same preparation or medicine, to detect different doses of this medicine in the body of the patient, which is of importance, for example, if a sequence of a building-up or a decaying dosage curve is to be reconstructed. By forming appropriate combinations, it is then also possible to detect both different medicines and different doses of the respective same medicine in the body of the patient and thus to distinguish them from each other.

For example, it is possible to distinguish two or three different drug doses in the GI tract from each other by the fact that their respective different resonance signals are selectively detectable. Since solid objects require a time interval of 12 hours and more to pass through the GI tract, as many as six drug doses can be present in the GI tract at any instant of monitoring during a long-time prescription of "twice daily".

If the drug doses are packed individually, such as, for example, in a blister or bubble pack, then the respective time of removal of a dose from the pack can additionally be documented, especially in a manner such as is described in West German Patent 3,335,301 or West German Offenlegungsschrifts 3,504,431 and 3,530,356. These items of information plus the subsequent detection or acquisition of the magnetic resonance signals of specific identity in each case in the body of the patient provide the evidence both for the exact time and for the verification of the, for example, oral application of a medicine.

Such provision of evidence is especially decisive or critical for certain drugs, for which a conscientious and faithful willingness by the patient to take them is essential for effective and safe therapy, and for which objective data relative to the "management" of the prescribed drugs are very important for the physician's evaluation with respect to the suitability of the dose and with respect to the degree of the drug effect produced by the actually taken dose.

The movements and forces of the human GI tract are known to be diverse and different and in particular to be capable of compacting, consolidating and compressing indigestible substances, although in similar manner they are also capable of dividing or dispersing these substances.

The latter capability is typically a function of the stomach and of the small intestine, and the former typically a function of the large intestine. According to a further embodiment of the invention it is therefore advantageous if the element formed from the respective magnetic material and contained in the associated preparation has a certain shape memory for its magnetically detectable, e.g., opened or unfolded or unrolled configuration, so that, for example, a few hours of maintenance of this magnetically detectable condition and thus a corresponding opportunity for accurate and reliable detection can be ensured. Preferably this shape memory is preadjustable.

However, a too strong shape memory intrinsically conceals the danger that the element formed from the magnetic material is too stiff, i.e., not sufficiently flexible, to pass safely through the GI tract, without causing the danger of an obstruction, an abrasion or even a perforation. This danger can be guarded against by appropriate configuration of the magnetic element, e.g., by attaching rounded or similarly shaped protective bodies at the respective ends of the element, e.g., wire, tape or strip. For example, the magnetic material in this connection can also be made in the form of a strip or wire of metallic glass with protective bodies at its ends.

According to a further embodiment of the invention, it can be advantageous to enclose the element formed from the magnetic material completely or partly in a soluble envelope and to add the element with its envelope to the preparation. Such an envelope can consist preferably of one material or several preselectable materials, each with dissolvability which differs in a manner which is specific to the region in the GI tract, e.g., with a specific dissolvability either only in the stomach or only in the small intestine or only in the large intestine, etc. Since the element is magnetically undetectable or is detectable in a completely different manner as long as it is still enclosed in its envelope, i.e., as long as this envelope has not yet dissolved, the possibility also exists in this case of combining, with the magnetic detectability of the element, its ability to be located in the course of its movement through the GI tract.

Moreover, the preparation according to the invention can be produced if desired in the form of a capsule, having segregated compartments for the pharmacologically active agent or agents and for the magnetic material(s).

Furthermore, the magnetically active substance or the element formed therefrom can additionally be disposed on a substrate.

Finally, the possibility also exists of surrounding the magnetic material or the element formed therefrom by a liquid-swellable material, especially by a water-swellable polymer. For practical purposes such a swellable material creates a type of tampon, which surrounds the magnetic material or element, whereby it is ensured that this element cannot cause any kind of injuries during its movement through the GI tract. Such a tampon can in particular be so formed that it initially surrounds, as a loose sheath, the magnetic element in its first, still unrolled condition, whereas in the next step it surrounds the then rolled-up element in appropriately crumpled manner, in order to occupy as little volume as possible. After the application, and at the instant at which the magnetic element is transformed to the magnetically detectable condition once the applied preparation has dissolved, e.g., the coil or roll has changed to a straightened or unrolled element, then the swellable magnetic coating, especially the water-swellable polymer sheath, can swell by absorbing the surrounding fluid, so that a preferably elongated protective element or protective tampon is produced, in the interior of which the magnetic material or element is contained, in the form, for example, of a tape or strip.

For more detailed explanation of the invention, its further features and advantages, the following description of exemplary embodiments in association with the drawings is provided.

The exemplary embodiments illustrated in FIGS. 1 to 9 and 11 to 14 are each shown in enlarged representation, in order to facilitate understanding of the present invention.

Figure 1:
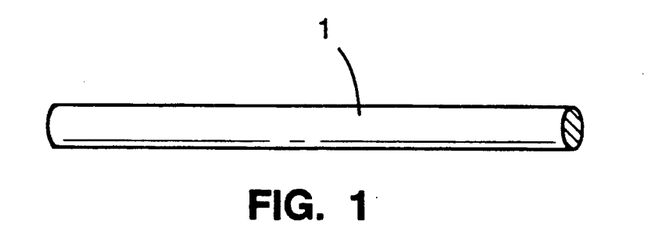
FIG. 1 shows a piece of a wire of a magnetic amorphous material.

FIG. 1 shows, for example, a piece of a wire 1, which consists of an amorphous metal or of an amorphous metal compound, i.e., of a material with such magnetic properties that it is capable of reacting to an externally acting magnetic field, which is generated, for example, by a monitoring device.

Figure 2:
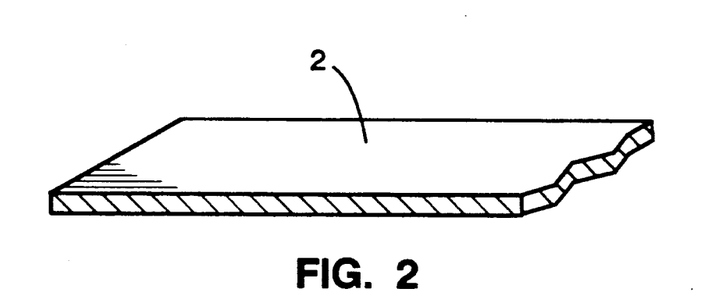
FIG. 2 shows a piece of a tape or strip of a magnetic amorphous material.

As shown in FIG. 2, an element in the form of a tape or strip 2 can also be formed, however, from the same material as used for forming a wire per FIG. 1, the possibility also existing of so minimizing the thickness dimension of such a strip or tape that an element in the form of a foil or a film is produced.

The further use of the wire illustrated in FIG. 1 or of the tape or strip illustrated in FIG. 2 in association with pharmaceutical preparations is explained in more detail by means of the subsequent figures.

Figure 3:
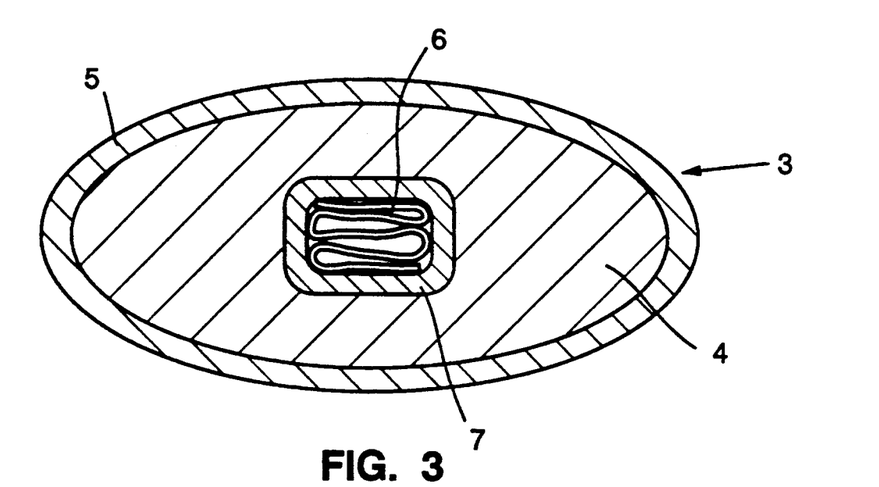
FIG. 3 shows a section through a pharmaceutical preparation or medicine in the form of a pill.

FIG. 3 shows a sectional view through a pill 3, which consists in the normal manner of one or more active substances 4, which are covered externally by a coating 5.

In the interior of this pill 3, i.e., inside the active substances 4, there is now additionally embedded an element 6, which is formed from a wire 1 per FIG. 1 or a tape or strip 2 per FIG. 2, more or less tightly folded in approximately zigzag manner. As FIG. 3 further shows, this element 6 can be disposed in an envelope 7 of, for example, rectangular cross section, this envelope 7 consisting, for example, of a material which can dissolve during passage through the GI tract, such as, for example, gelation or the like. However, the envelope 7 can also consist of a material which exhibits a solubility which differs in a manner specific to the GI region, i.e., either the small intestine or the large intestine, for example, is predestined as the location of dissolution.

Furthermore, the envelope 7 can also be so formed that it only partly surrounds the element 6.

Figure 4:
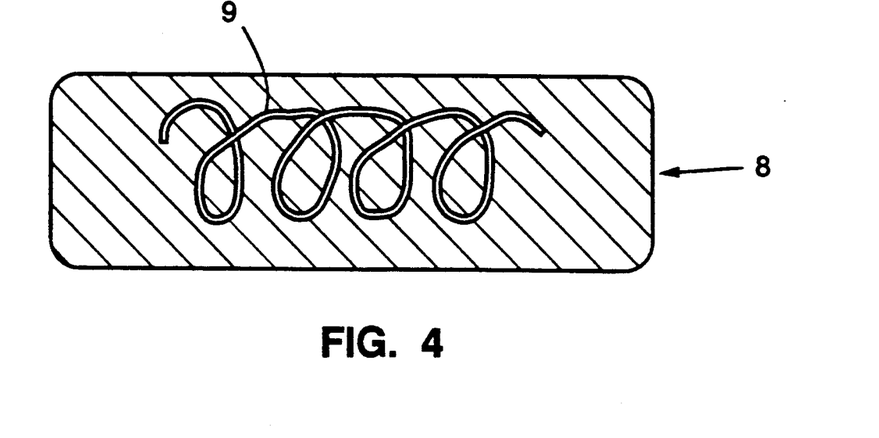
FIG. 4 shows a section through a medicine in the form of a tablet.

FIG. 4 shows a side view through a medicine in the form of administration of a tablet 8, in the interior of which there is embedded an element 9, which consists of a wire 1 per FIG. 1 bent in helical manner.

Figure 5:
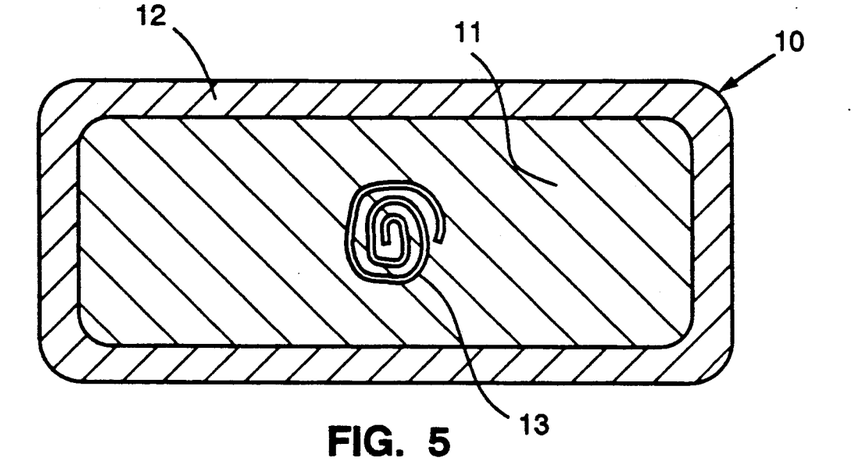
FIG. 5 shows a section through a medicine in the form of a capsule.

FIG. 5 shows a side view through a further medicine, which is made in the form of a capsule 10, in which an active substance or a combination of active substances 11 is contained inside an envelope 12, which consists, for example, of gelatin. Furthermore, an element 13, which is formed from a tape or band 2 per FIG. 2 assembled in coiled or rolled manner, is embedded in the interior of the capsule 10 inside the active substances 11.

Figure 6:
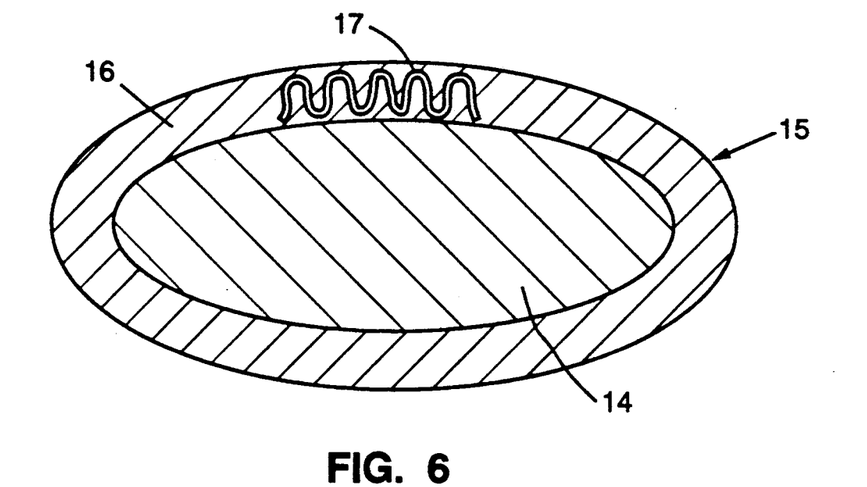
FIG. 6 shows a section through a medicine in the form of a sugar-coated pill.

FIG. 6 shows a side view of a sugar-coated pill 15, in which the active substance or the active substances 14 are covered externally by a relatively thick coating 16.

In this case the possibility exists of placing, inside the coating 16 of the sugar-coated pill 15, a magnetic element 17, which in a manner similar to that of the element 6 per FIG. 3 can consist of a wire 1 per FIG. 1 bent or folded together in zigzag manner.

Figure 9:
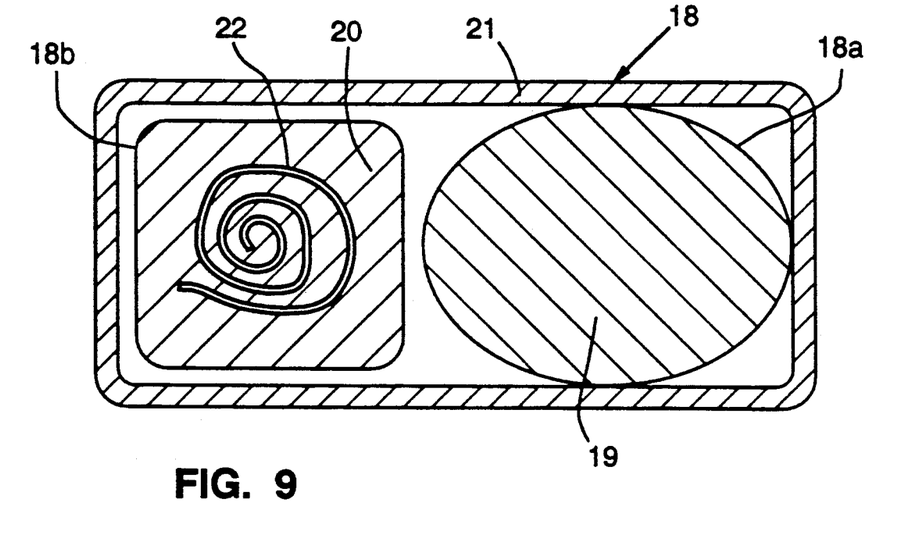
FIG. 9 shows a section through a further medicine in a further capsule-type embodiment.

Furthermore, FIG. 9 shows a side view through a medicine which, in a manner similar to that illustrated in FIG. 5, has the configuration or external shape of a capsule. In the exemplary embodiment per FIG. 9, however, the capsule contents are divided into a first part 18a and a second part 18b, these two parts 18a and 18b being enclosed externally by a common capsule sheath 21.

The first part 18a of the capsule contents in this case contains an active substance or active substances 19, whereas in the second part 18b of the capsule's contents there is placed a magnetic element 22, which is formed in a manner similar to that of the element 13 per FIG. 5.

Preferably the element 22 per FIG. 9 is located inside an embedding medium 20, which, together with an envelope which is formed in a manner approximately similar to that of the envelope 7 per FIG. 3, for practical purposes forms the second part 18b of the contents of the capsule 18, this medium being particularly biologically inert and nontoxic.

In similar manner, an envelope 7, as explained by means of FIG. 3, can also be provided for the elements 9 (per FIG. 4) or 13 (per FIG. 5) or 17 (per FIG. 6).

It is understood that various magnetic materials with appropriately different magnetic properties can be provided for the elements 6 (per FIG. 3) or 9 (per FIG. 4) or 13 (per FIG. 5) or 17 (per FIG. 6) or 22 (per FIG. 9). In this connection the most diverse combinations of materials/material properties with geometric forms of the elements of the most diverse type are possible.

Nevertheless, it is common to all elements 6, 9, 13, 17 or 22 that, after dissolution of the associated preparation or medicine in the GI tract, they are transformed or restored to an opened initial condition in which the said elements once again assume the configuration of a straightened wire or strip or tape or film, so that the said elements exhibit the desired magnetic resonance properties only in this magnetically detectable condition or in this configuration, whereby the detectability of these elements by means of an externally acting magnetic field is ensured, as has already been explained in detail hereinbefore.

Figure 10:
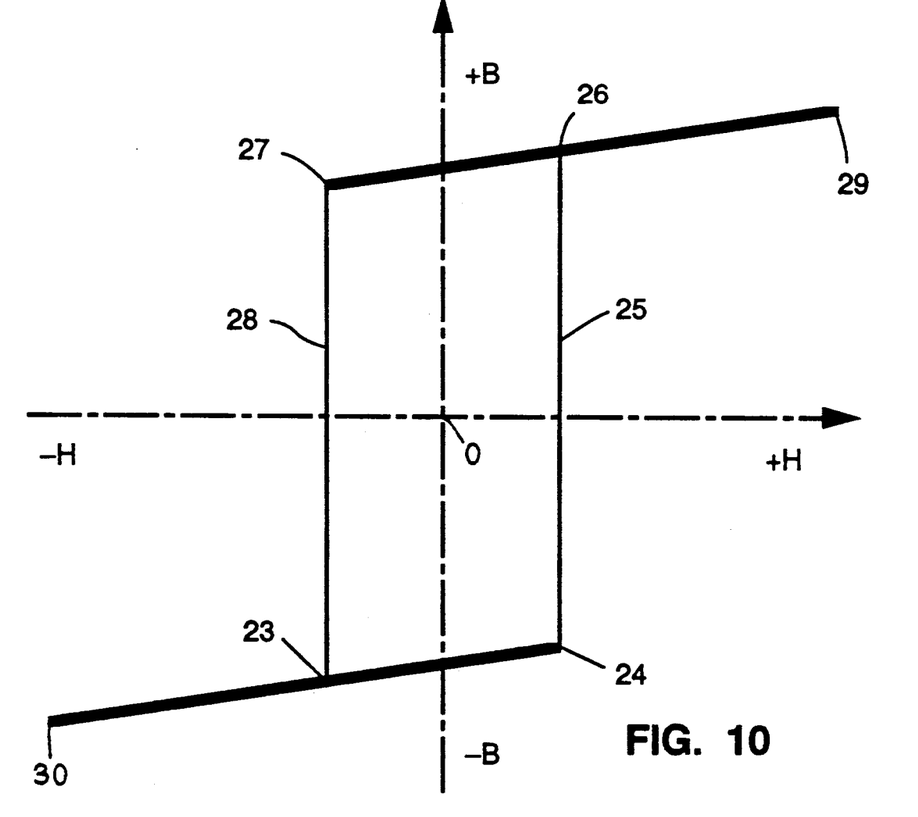
FIG. 10 shows a hysteresis loop for explanation of the magnetic properties of the material added to the medicines.

The magnetic materials, or the elements formed therefrom, incorporated into the present pharmaceutical compositions preferably exhibit a magnetization curve such as is illustrated, for example, in FIG. 10. For clarity, this diagram contains a hysteresis loop shown in simplified form, with the magnetic field strength H on the abscissa and the magnetic induction B on the ordinate. H thus represents the externally acting magnetic field.

The negative maximum induction point ($-B_{max}$) is indicated with 23, the positive threshold value of the magnetic field with 24, the positive maximum induction point ($+B_{max}$) with 26 and the negative threshold value of the magnetic field with 27. When the magnetic field reaches the point 24 and exceeds it, an abrupt regenerative reversal of the polarity occurs, so that the point 26 ($+B_{max}$) on the hysteresis loop is reached. The line 25 between the points 24 and 26 therefore represents a large Barkhausen jump, according to which the polarity reversal occurs.

If on the other hand the magnetic field H passes in reversed direction through the zero point and proceeds further in the negative direction, the point 27, i.e., the negative threshold value of the magnetic field is ultimately reached, from which an abrupt regenerative reversal of the polarity again occurs, until the point 23 ($-B_{max}$) is reached. The line 28 between the points 27 and 23 in turn represents the new large Barkhausen jump in this region.

Furthermore, the points of positive saturation and negative saturation are indicated with 29 and 30 respectively on the magnetization curve per FIG. 10.

The hysteresis loop characteristic of the respective magnetic material is dependent on the special material composition and on the particular geometric forms and dimensions of the element formed therefrom.

Figure 7:
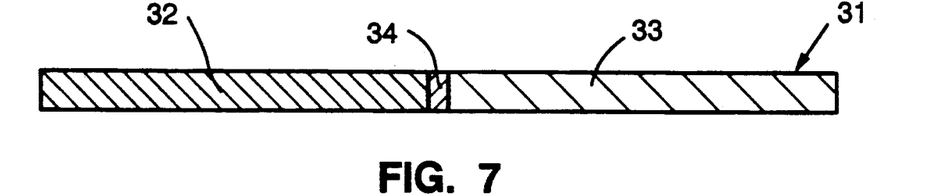
FIGS. 7 and 8 each show a section through elements formed from magnetic material, in different embodiments.
Figure 8:
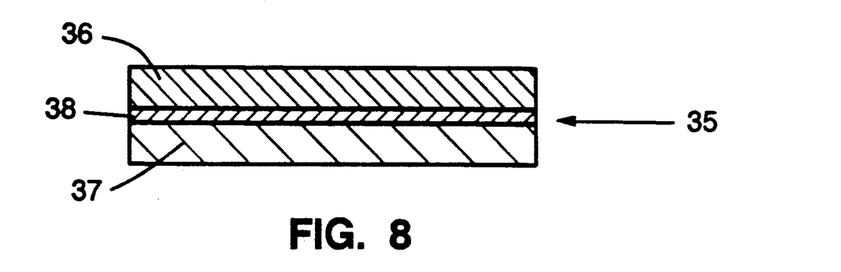

As can be seen from FIGS. 7 or 8, the possibility also exists of initially forming a first composite element 31 or a second composite element 35, which can be added respectively, for example to one of the medicines illustrated in FIGS. 3 to 6 or 9 instead of the magnetic elements shown therein.

In the condition shown in FIGS. 7 or 8, the composite elements 31 or 35 are located in each case in a magnetically undetectable condition, and more precisely because of the fact that a first partial element 32 of a magnetically soft material is combined with a second partial element 33 of a magnetically hard material by means of a connecting layer 34 in regions facing each other in end-to-end manner to obtain the already mentioned composite element 31 (FIG. 7), or because of the fact that—in the manner of a stacking of layers—a first plate-like or foil-like component 36 of a magnetically soft material is combined with a second correspondingly shaped component 38 in the form of a connecting layer to obtain the already mentioned second composite element 35 (FIG. 8).

The connecting layers 34 and 38 in the composite elements 31 and 35 respectively consist of a material which in each case can be dissolved by the gastric juices or enzymes, so that the respective composite element 31 or 35, after dissolution, in the GI tract, of the associated preparation administered to a patient, is transformed to a condition which is magnetically detectable for the electronic monitoring device by the fact that the partial elements 33 (FIG. 7) or the components 37 (FIG. 8) become detached or separated from the respective composite element 31 or 35 as a result of dissolution of the layers 34 or 38.

Consequently, for the first partial element 32 of the composite element 31 per FIG. 7 or for the first component 36 of the composite element 35 per FIG. 8 there is established in each case a magnetically detectable condition, in which the desired magnetic properties of the partial element 32 or of the component 36 become fully effective, so that, for example, by means of an external alternating magnetic field, which is generated by the electronic monitoring device, the corresponding detection possibilities relative to the applied preparation are once again obtained.

Figure 11:
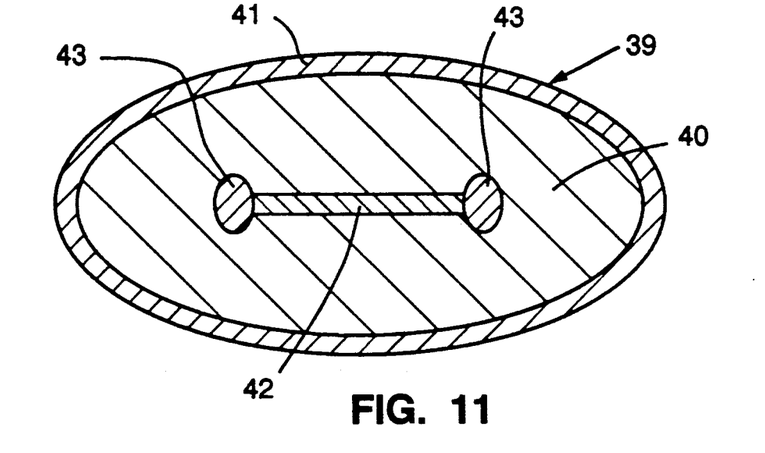
FIG. 11 shows a section through a further medicine in the form of a pill.

FIG. 11 shows an exemplary embodiment of a pharmaceutical preparation in the form of a further pill 39, which essentially consists of an inner part containing the active substance or substances 40 and a coating 41 applied thereon. In the interior part of the pill 39 there is once again placed a sixth element 42 formed from a magnetic material, which in the present exemplary embodiment has the configuration of a short, straightened wire, tape or strip. At each of the ends of the element 42 there are located ball-shaped or similarly formed protective bodies 43 of a suitable, for example, elastically deformable and otherwise inert material, such that no danger whatsoever of injuries due to the element 42 of magnetic material occurs in the region of the stomach or intestinal walls after dissolution of the applied preparation in the GI tract.

Figure 12:
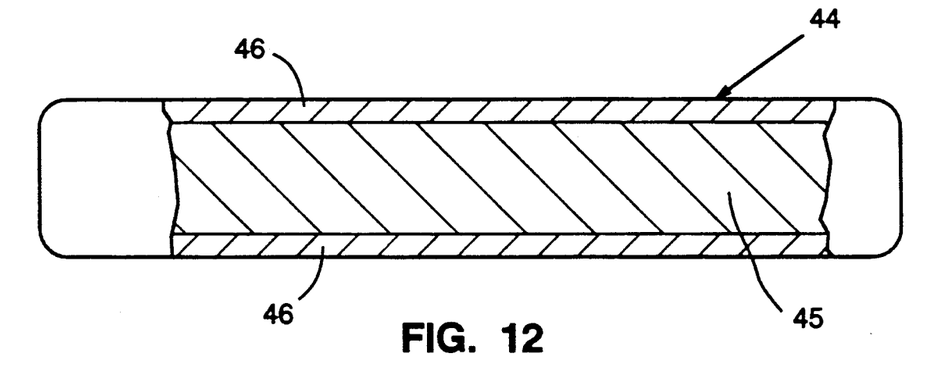
FIG. 12 shows a partial sectional view of a further element formed from magnetic material.

Furthermore, FIG. 12 shows an exemplary embodiment for a further, seventh element 44 formed from a magnetic material 45, the surfaces of which are coated with a protective layer 46 which cannot be dissolved or attacked by the gastric juices or enzymes, so that the entire element 44 is biologically inert and nontoxic.

Instead of this it would also be possible to select a magnetic material 45 with such a composition that it cannot be dissolved or attacked by the gastric juices and is otherwise biologically inert, and above all nontoxic.

Figure 13A:
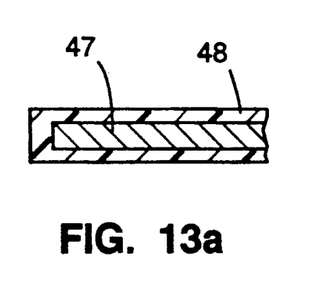
FIGS. 13a and 13b each show a partial sectional view through an element consisting of magnetic material, according to a further embodiment.
Figure 13B:
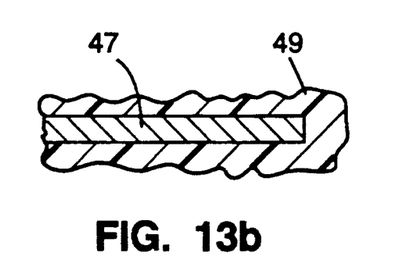

FIG. 13a shows a sectional view through a further partly illustrated element of a magnetic material 47, the surface of which is surrounded by a water-swellable polymer sheath 48. After dissolution, in the GI tract of the patient, of the applied medicine containing the material 47, a condition is established which is evident from FIG. 13b and in which the original polymer sheath 48 has changed to a liquid-swollen sheath 49, so that a quasi-elongated tampon is formed from the magnetic material, in such a manner that no danger whatsoever of injury in the interior region of the gastrointestinal tract can occur as a result of the application.

Figure 14:
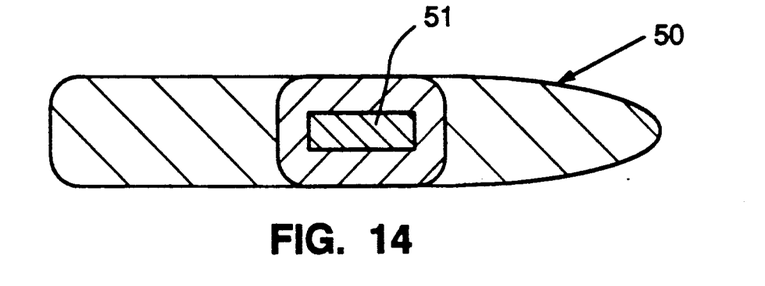
FIG. 14 shows a side view of a medicine in the form of a suppository.

Finally, FIG. 14 shows another exemplary embodiment of a medicine in the form of a suppository 50, in the interior of which an eighth element 51 formed from magnetic material is placed, in a manner corresponding to that already explained by means of the exemplary embodiments per FIGS. 3 to 6, 9 or 11.

I claim:

1. A pharmaceutical composition in unit dosage form for administration to the gastrointesinal tract of a patient comprising a pharmacologically active agent and a magnetic material, said magnetic material, when present in the gastrointestinal tract of the patient, being capable of reacting to an externally applied magnetic field to produce a magnetic signal which is selectively detectable by an electronic monitoring device, and thereby providing verification that the composition is present in the patient's gastrointestinal tract and further providing an indication of the location of the composition in the patient's gastrointestinal tract, the magnetic material being a material which exists prior to administration of the composition to the patient's gastrointestinal tract in a first state which does not produce the selectivity detectable magnetic signal but which undergoes transformation in the gastrointestinal tract, as a result of the action of the gastrointestinal environment, to a second state which does produce the selectively detectable magnetic signal, the magnetic material being a wire, tape, strip or film which in the first state is folded into a magnetically undetectable configuration and which in its second state is unfolded into a magnetically detectable configuration.

2. The composition of claim 1 wherein said magnetic material is comprised of magnetically soft material.

3. The composition of claim 1 wherein said magnetic material is comprised of an amorphous material.

4. The composition of claim 3, wherein said amorphous material is an amorphous metal.

5. The composition of claim 1, wherein said amorphous material is an amorphous iron-silicate-boron-carbon compound.

6. The composition of claim 1, wherein said magnetic material is biologically inert and nontoxic.

7. The composition of claim 1, wherein said composition is in a unit dosage form selected from the group consisting of a pill, lozenge, tablet, capsule, film- or membrane-coated tablet or capsule, sugar-coated pill, and suppository.

8. The composition of claim 1, wherein said magnetic material is present in a layer which coats said pharmacologically active agent.

9. The composition of claim 1 wherein said magnetic material has a shape memory for its magnetically detectable second state configuration.

10. The composition of claim 9, wherein the shape memory is preadjustable.

11. The composition of claim 1 wherein said magnetic material is completely or partly enclosed in an envelope comprised of a biodegradable material.

12. The composition of claim 1, wherein said magnetic material and said pharmacologically active agent are contained within a capsule having segregated compartments therefor.

13. The composition of claim 1, wherein said magnetic material is disposed on a substrate.

14. The composition of claim 1, wherein said magnetic material is encapsulated in a water-swellable polymer.

15. A method of determining whether or not a patient has taken a gastrointestinal tract administered pharmaceutical composition unit dosage form of claim 1, comprising the steps of:

subjecting said patient to an externally applied alternating magnetic field, selectively detecting the presence or absence of said magnetic signal, and relating the presence of said magnetic signal to the fact that the patient had taken the pharmaceutical composition unit dosage form and the absence of said magnetic signal to the fact that the patient had not taken the pharmaceutical composition unit dosage form.

* * * * *